(12) United States Patent
Yamada et al.

(10) Patent No.: US 8,976,354 B2
(45) Date of Patent: Mar. 10, 2015

(54) POLARIZATION STATE MEASUREMENT APPARATUS AND POLARIZATION STATE MEASUREMENT METHOD

(75) Inventors: Hideaki Yamada, Shimosuwa-machi (JP); Michihiro Nagaishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 316 days.

(21) Appl. No.: 13/564,053

(22) Filed: Aug. 1, 2012

(65) Prior Publication Data

US 2013/0033707 A1     Feb. 7, 2013

(30) Foreign Application Priority Data

Aug. 5, 2011   (JP) .................................. 2011-171535

(51) Int. Cl.
| | |
|---|---|
| G01J 4/00 | (2006.01) |
| G01N 21/21 | (2006.01) |
| G01J 4/04 | (2006.01) |
| G01N 21/19 | (2006.01) |

(52) U.S. Cl.
CPC . G01N 21/21 (2013.01); G01J 4/04 (2013.01); *G01N 21/19* (2013.01)
USPC ........... 356/364; 356/366; 356/367; 356/368; 356/370

(58) Field of Classification Search
CPC ....... G01N 21/21; G01N 21/19; G01N 21/23; G01N 33/5432; G01N 33/5438; G01N 33/544; G01N 33/54373
USPC .......................... 356/364, 366, 367, 368, 370
See application file for complete search history.

(56) References Cited

U.S. PATENT DOCUMENTS

| | | | | |
|---|---|---|---|---|
| 3,450,478 | A | * | 6/1969 | Sebestyen ...................... 356/365 |
| 4,076,420 | A | * | 2/1978 | De Maeyer et al. ............ 356/73 |
| 4,309,110 | A | * | 1/1982 | Tumerman ..................... 356/365 |
| 2004/0008348 | A1 | * | 1/2004 | Kishikawa et al. ........... 356/364 |
| 2007/0296973 | A1 | * | 12/2007 | Kiers et al. .................... 356/369 |
| 2010/0245822 | A1 | * | 9/2010 | Garab et al. .................. 356/365 |

FOREIGN PATENT DOCUMENTS

| | | |
|---|---|---|
| JP | 2004-340833 A | 12/2004 |
| JP | 2007-093289 A | 4/2007 |
| JP | 4186189 B2 | 11/2008 |
| WO | WO-2007/029652 A1 | 3/2007 |

* cited by examiner

*Primary Examiner* — Tarifur Chowdhury
*Assistant Examiner* — Sunghee Y Gray
(74) *Attorney, Agent, or Firm* — Global IP Counselors, LLP

(57) ABSTRACT

An optical apparatus has a light detecting section which detects light and emits transmitted light where linearly polarized light, which is converted by a polarizing section, is transmitted through a subject. In addition, the optical apparatus has an orthogonal separating section which orthogonally separates the emitted light from the light detecting section and a light reception section which receives light which is orthogonally separated by the orthogonal separating section. A calculation apparatus outputs a rotation control signal to a rotation apparatus and rotation controls the light detecting section so that the rotation plane is orthogonal with regard to an optical path of the transmitted light. Then, the calculation apparatus measures the polarization state of the transmitted light, which is transmitted through the subject S using the intensity with which the light, is received by the light receiving section.

8 Claims, 8 Drawing Sheets

POLARIZATION STATE MEASUREMENT APPARATUS AND POLARIZATION STATE MEASUREMENT METHOD

CROSS-REFERENCE TO RELATED APPLICATIONS

This application claims priority to Japanese Patent Application No. 2011-171535 filed on Aug. 5, 2011. The entire disclosure of Japanese Patent Application No. 2011-171535 is hereby incorporated herein by reference.

BACKGROUND

1. Technical Field

The present invention relates to an apparatus, which measures a polarization state of transmitted light where linearly polarized light is transmitted through a subject, or the like.

2. Background Technology

It is possible to know the state of a substance without directly touching the substance, by measuring light which is transmitted through the substance. For example, when linearly polarized light passes through an optically active substance such as glucose, a property referred to as optical rotation where the polarization plane thereof is rotated is known. The linearly polarized light is a combination of left and right circularly polarized light. Since the refractive indexes of the left and right circularly polarized light are different, a difference occurs in the speed of the left and right circularly polarized light which travels in the substance. As a result, a phase difference occurs in the left and right circularly polarized light which passes through a subject and the polarization plane is rotated in the light which is composed of the left and right circularly polarized light.

In addition, when linearly polarized light is incident onto a substance (a chiralic substance) where the absorption rates with regard to left and right circularly polarized light are different, the amplitude of the light of the left and right circularly polarized light (the magnitude of the light) changes due to a characteristic referred to as circular dichroism. Due to optical rotation and circular dichroism, the transmitted light which is transmitted through the substance becomes elliptically polarized light where the polarization plane has been rotated from when incident. The techniques for measuring the polarization state which focuses on optical rotation and circular dichroism are disclosed in, for example, patent literature 1 to 3.

International Patent Publication No. 2007/029652 (Patent Document 1), Japanese Laid-open Patent Application No. 2007-93289 (Patent Document 2) and Japanese Laid-open Patent Application No. 2007-340833 (Patent Document 3) are examples of the related art.

SUMMARY

Problems to Be Solved By the Invention

For example, in the technique disclosed in PTL2, light which has various phase differences is incident onto a subject by light which has passed through a liquid crystal element being incident onto a subject and a voltage applied with regard to a liquid crystal element being controlled. Then, the polarization state of the subject is measured by detecting the intensity of the light with each of the phase differences transmitted through the subject. However, since the temperature dependence of the liquid crystal element which creates the phase differences is high, there is a problem in that the measurement accuracy of the polarization state is reduced if measurement is not performed in a state where a constant temperature is maintained.

In addition, in the technique disclosed in PTL3, light, which includes equal amounts of left and right circularly polarized light, is irradiated onto a subject. Then, the transmitted light which is transmitted through the subject is orthogonally separated into left and right circularly polarized light and the circular dichroism of the subject is evaluated by detecting the light intensity of the polarized light which has been orthogonally separated. However, the method of PTL3 presupposes an ideal state where there are absolutely no errors in relation to an optical system such as accuracy of polarizers or prisms which configure the optical system or errors in assembly (referred to below in total as "optical system errors"). A state where there are absolutely no optical system errors is not attainable in practice. In addition, in the measurement of the polarization state, it is necessary to grasp slight changes in the light intensity of the transmitted light which is transmitted through the subject and it is not possible to ignore the optical system errors since a slight optical system error translates to measurement error.

The present invention takes into consideration the problems described above and the object thereof is to propose a novel technique for measuring the polarization state of transmitted light which is transmitted through a subject.

Means Used to Solve the Above-Mentioned Problems

A first embodiment for solving the problems described above is a polarization state measurement apparatus which is provided with a light detecting section which detects light and emits transmitted light where linearly polarized light is transmitted through a subject, an orthogonal separating section which orthogonally separates the emitted light from the light detecting section, a light reception section which receives light which is orthogonally separated by the orthogonal separating section, a rotation control section which rotates the light detecting section so that the rotation plane is orthogonal with regard to an optical path of the transmitted light, and a polarization state measuring section which measures the polarization state of the transmitted light using the intensity with which the light, which is orthogonally separated during the rotation of the light detecting section, is received by the light receiving section.

In addition, a polarization state measuring method, which is a method for measuring the polarization state of transmitted light by controlling an optical apparatus provided with a light detecting section which detects light and emits the transmitted light where linearly polarized light is transmitted through a subject, an orthogonal separating section which orthogonally separates the emitted light from the light detecting section, and a light reception section which receives light which is orthogonally separated by the orthogonal separating section, may be configured as another embodiment to include rotating the light detecting section so that the rotation plane is orthogonal with regard to an optical path of the transmitted light and measuring the polarization state of the transmitted light using the intensity with which the light, which is orthogonally separated during the rotation of the light detecting section, is received by the light receiving section.

According to the first embodiment and the like, the light detecting section is rotated so that the rotation plane is orthogonal with regard to the optical path of the transmitted light. Then, the polarization state of the transmitted light, which is transmitted through the test body, is measured using the intensity with which the light, which is orthogonally separated during the rotation of the light detecting section, is received by the light receiving section. The transmitted light where linearly polarized light is transmitted through the subject becomes elliptically polarized light where the polarization plane has been rotated using the circular dichroism and optical rotation of the subject. It is possible to measure the polarization state of the transmitted light which is transmitted through the subject by observing the locus which is drawn out by the intensity with which the light, which is orthogonally separated during the rotation of the light detecting section, is received by the light receiving section. In addition, in this configuration, it is possible to also compensate for the optical system errors since it is possible to grasp the optical system errors, which are caused by accuracy of polarizers or prisms which configure the optical system, errors in the assembly, and the like, in a form of the locus which is drawn out by the intensity of the light which is received by the light receiving section.

In addition, a polarization state measurement apparatus may be configured as a second embodiment so that the rotation control section of the polarization state measurement apparatus of the first embodiment rotates the light detecting section within a predetermined angular range.

According to the second embodiment, the rotation control section rotates the light detecting section within the predetermined angular range. It is sufficient if the predetermined angular range is an angular range where, for example, it is possible to confirm an apex in the longitudinal direction and an apex in the latitudinal direction of the locus which is drawn out by the intensity of the light which is received by the light receiving section. Due to the light detecting section being rotated within the angular range, it is possible to measure the polarization state of the transmitted light which is transmitted through the subject.

In addition, a polarization state measurement apparatus may be configured as a third embodiment so that the polarization state measuring section of the polarization state measurement apparatus of the first or second embodiment has a vibration locus determining section which determines a vibration locus of the transmitted light using the intensity of the light which is received and measures the polarization state of the transmitted light using the vibration locus which is determined by the vibration locus determining section.

According to the third embodiment, the vibration locus of the transmitted light is determined using the intensity of the light which is received. The vibration locus of the transmitted light is a locus which represents the vibration direction of the transmitted light which is elliptically polarized light. The vibration locus of the transmitted light is determined using the intensity with which the light, which is orthogonally separated during the rotation of the light detecting section, is received by the light receiving section. Then, it is possible to accurately perform the measurement of the polarization state of the transmitted light by using the vibration locus which is determined.

In addition, a polarization state measurement apparatus may be configured as a fourth embodiment so that the polarization state measuring section of the polarization state measurement apparatus of any one of the first to the third embodiments measures the polarization state by the transmitted light being assumed to be elliptically polarized light and the feature values of ellipses being measured.

According to the fourth embodiment, the transmitted light is assumed to be elliptically polarized light and the feature values of ellipses are measured. Examples of the feature values of an ellipse include, for example, the length of the major axis and the minor axis of the ellipse. It is possible to correctly grasp the form of elliptically polarized light by measuring these feature values.

In addition, a polarization state measurement apparatus may be configured as a fifth embodiment so that the linearly polarized light of the polarization state measurement apparatus of any one of the first to the fourth embodiments has a deflection angle of 45°.

According to the fifth embodiment, by setting the deflection angle of the linearly polarized light which is incident onto the subject to 45°, it is possible to grasp a slight change in the intensity with which the light, which has been orthogonally separated by the orthogonal separating section, is received by the light receiving section and measure the polarization state with high accuracy.

In addition, a polarization state measurement apparatus may be configured as a sixth embodiment so that the light detecting section of the polarization state measurement apparatus of any one of the first to the fifth embodiments has a Glan-Thompson prism.

According to the sixth embodiment, since the light detecting section has a Glan-Thompson prism, high polarization purity (which can also be referred to as the purity of the light detection in this case) can be obtained.

In addition, a polarization state measurement apparatus may be configured as a seventh embodiment so that the orthogonally separating section of the polarization state measurement apparatus of any one of the first to the sixth embodiments has a Wollaston prism.

According to the seventh embodiment, since the orthogonally separating section has a Wollaston prism, it is possible to simply and appropriately orthogonally separate the linearly polarized light which is emitted from the light detecting section.

BRIEF DESCRIPTION OF THE DRAWINGS

Referring now to the attached drawings which form a part of this original disclosure.

DETAILED DESCRIPTION OF EXEMPLARY EMBODIMENTS

An embodiment will be described where the present invention is applied to a polarization state measurement apparatus which measures the polarization state of transmitted light of a subject using an optical apparatus. Here, naturally, the embodiments where the present invention can be applied are not limited to the embodiment described below.

Figure 1:
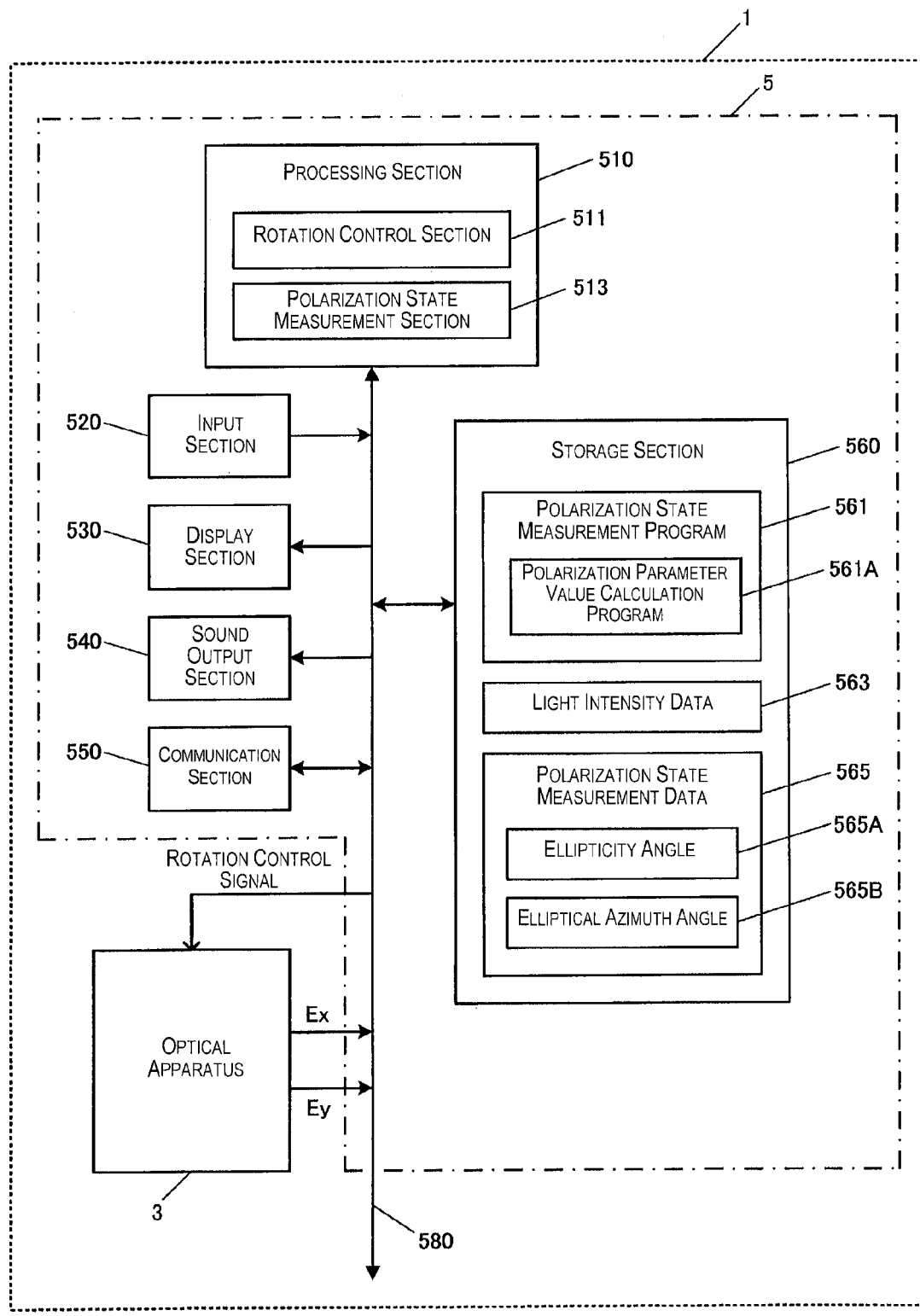
FIG. 1 is a block diagram illustrating a functional configuration of a polarization state measurement apparatus.

FIG. 1 is a block diagram illustrating an example of a functional configuration of a polarization state measurement apparatus 1 of the present embodiment. The polarization state measurement apparatus 1 is configured by being provided with an optical apparatus 3 and a calculation apparatus 5 as a main configuration. The polarization state measurement apparatus 1 is, for example, used by being built into a measurement unit such as a sugar content measurement apparatus which measures the sugar content of fruit or a blood sugar level measurement apparatus which measures the blood sugar level of a person.

1. Configuration of Optical Apparatus

Figure 2:
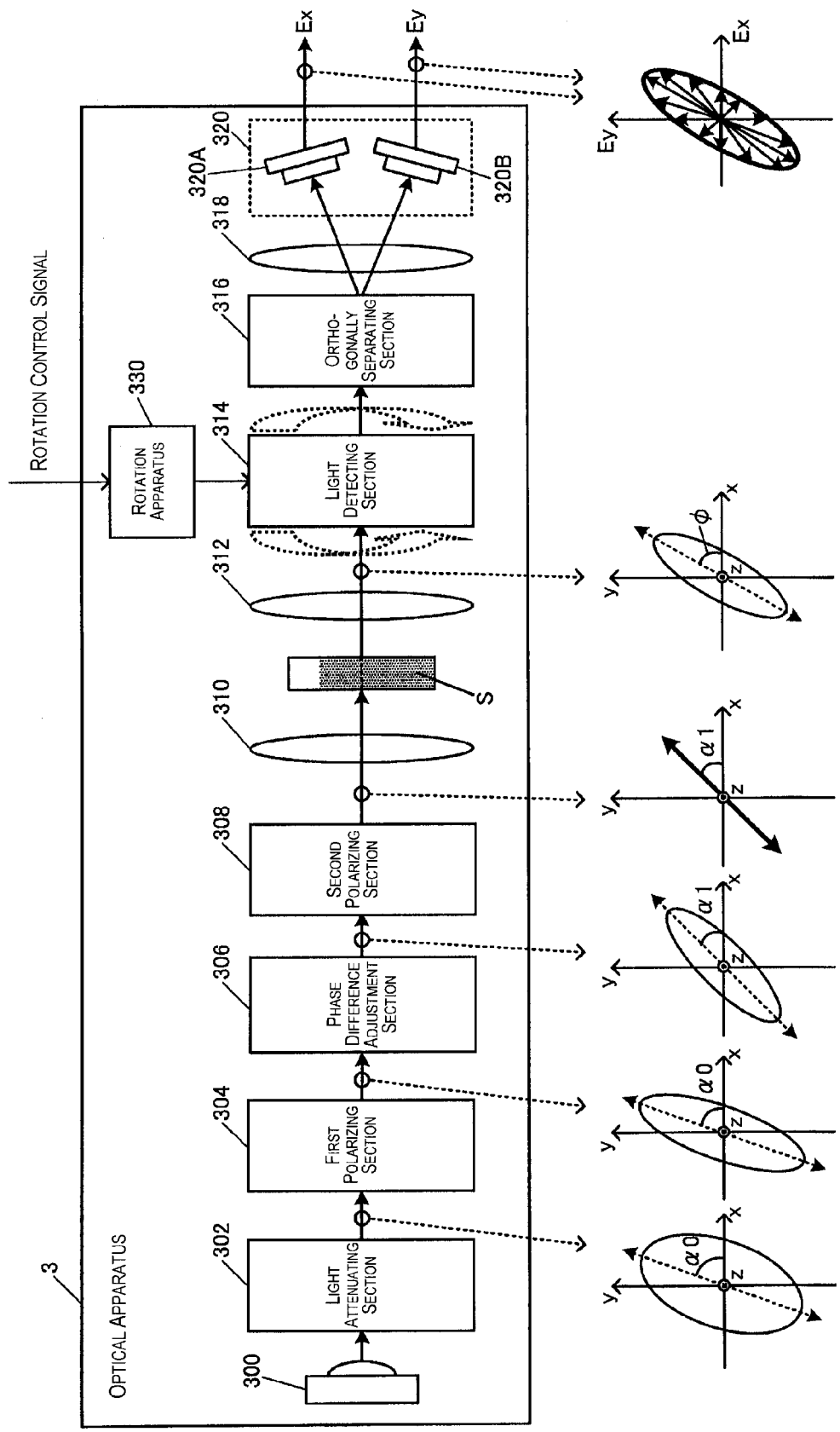
FIG. 2 is a configuration diagram of an optical system which configures an optical apparatus.

FIG. 2 is a diagram illustrating an outline of an optical configuration of an optical apparatus 3. The optical apparatus 3 is configured to have, for example, a light source 300, a light attenuating section 302, a first polarizing section 304, a phase difference adjustment section 306, a second polarizing section 308, a first light concentrating section 310, a second light concentrating section 312, a light detecting section 314, an orthogonally separating section 316, a third light concentrating section 318, a light receiving section 320, and a rotation apparatus 330.

A subject S is arranged between the first light concentrating section 310 and the second light concentrating section 320. It is possible for the subject S to be an arbitrary sample such as a solid or a liquid which contains an optically active substance. In the present embodiment, the subject S is a reagent with glucose as a main component. The present embodiment is where the polarization state of the transmitted light which is transmitted through the subject S is measured in order to evaluate the circular dichroism and the optical rotation of the sample S.

The light source 300 is an apparatus which generates and emits light and is configured to have, for example, a semiconductor laser (laser diode). The light source 300 radiates laser light, which is light aligned to the phase of a predetermined wavelength (for example, 650 nanometers [nm]), from an edge surface which is a half mirror.

The light attenuating section 302 is an element which reduces the amount of light which is radiated from the light source 300, and for example, is configured to have, for example, an optical filter such as a ND (Neutral Density) filter.

The first polarizing section 304 is an element (polarizer) which converts the light which is attenuated by the light attenuating section 302 to linearly polarized light and is configured to have, for example, a polarizing optical element such as a polarizing prism.

The phase difference adjustment section 306 is an element (phase element) which adjusts the phase difference of the emitted light of the first polarizing section 304 and is configured to have, for example, a retardation plate such as a wavelength plate. In the present embodiment, the phase difference adjustment section 306 has a ½ wavelength plate.

The second polarizing section 308 is an element (polarizer) which converts the polarized light, where the phase difference is adjusted by the phase difference adjustment section 306, into linearly polarized light and is configured to have, for example, a polarizing optical element such as a polarizing prism. In the present embodiment, the second polarizing section 308 has a Glan-Thompson prism which is one type of Glan type polarizer.

The first light concentrating section 310 is an element which concentrates linearly polarized light which is incident from the second polarizing section 308 and is configured to have, for example, a light concentrating lens. The light which is concentrated by the first light concentrating section 310 is incident onto the subject S.

The second light concentrating section 312 is a lens which concentrates transmitted light which is transmitted through the subject S and the light which is concentrated by the second light concentrating section 312 is incident onto the light detecting section 314.

The light detecting section 314 is an element (light detecting element) which detects the transmitted light which is concentrated by the second light concentrating section 312 and is configured to have, for example, a polarizing optical element such as a polarizing prism. In the present embodiment, the light detecting section 314 has a Glan-Thompson prism in the same manner as the second polarizing section 308.

In addition, the light detecting section 314 rotates along the vertical direction (circumferential direction of the light detecting element) with regard to the incidence direction of the light according to the rotational driving of the rotation apparatus 330. That is, the rotation apparatus 330 rotates the light detecting section 314 so that the rotation plane is orthogonal with regard to the optical path of the transmitted light which is transmitted through the subject S. The rotation apparatus 330 is, for example, an apparatus which has a rotation mechanism such as a stepping motor which rotates only a certain angle each time a pulse voltage is applied and rotationally drives the light detecting section 314 according to a rotation control signal which is output from the calculation apparatus 5.

The orthogonally separating section 316 is an element which separates the linearly polarized light which is incident from the light detecting section 314 into orthogonal components which are made up of predetermined aperture angles. In the present embodiment, the orthogonally separating section 316 has a Wollaston prism which is one type of polarizing optical element.

The third light concentrating section 318 is a light concentrating lens which concentrates linearly polarized light which is orthogonally separated by the orthogonally separating section 316. The linearly polarized light which is concentrated by the third light concentrating section 318 is incident onto the light receiving section 320.

The light receiving section 320 is an element which receives linearly polarized light which is orthogonally separated by the orthogonally separating section 316 and is concentrated by the third light concentrating section 318 and is configured to have a light detecting unit such as a photodiode. The light receiving section 320 has a first light receiving section 320A and a second light receiving section 320B, detects polarized light components orthogonal to each other (a P component and an S component) which are orthogonally separated by the orthogonally separating section 316, and outputs voltage values according to the light intensity thereof to the calculation apparatus 5 as detection voltages ($E_x$, $E_y$).

2. Principles

In the lower portion of FIG. 2, the polarization state of the light, which is emitted from each of the configuration sections of the optical apparatus 3, is schematically drawn. In the present embodiment, the travelling direction of the emitted light from the light source 300 is set as the z axis, and in the lower portion of FIG. 2, the front and back direction where the forward direction toward the page surface is positive is shown as the z axial direction. In addition, the surface which includes the travelling direction of the light and a magnetic field is shown as a zy plane, the surface which includes the travelling direction of the light and an electric field is shown as a zx plane, and a xy plane which is orthogonal thereto is shown a plane in an up/down and left/right direction. In addition, in the xy plane, elliptically polarized light is shown using elliptical shapes and linearly polarized light is shown using vectors with linear shapes.

The light, which is emitted from the light source 300 and attenuated by the light attenuating section 302, is, for example, elliptically polarized light which is close to linearly polarized light where the deflection angle is set as "α0", in other words, approximate to linearly polarized light. Here, in FIG. 2, the angle, which the electric field vector of the polarized light forms with the x axis, is defined as the deflection angle "α". The elliptically polarized light with the deflection angle "α0" is converted to elliptically polarized light which is even closer to linearly polarized light by the first polarizing section 304. That is, as shown in FIG. 2, the elliptically polarized light, where the length in the minor axis of the ellipse is slightly shortened, is emitted from the first polarizing section 304 with the deflection angle "α0" as it is without being changed.

The phase difference in the emitted light from the first polarizing section 304 is adjusted using the phase difference adjustment section 306. In the present embodiment, the phase difference adjustment section 306 has a ½ wavelength plate. As a result, the rotation plane of the polarized light, which is incident onto the phase difference adjustment section 306, is rotated. That is, in a case where the angle, which is formed by the polarization direction of the incident light and the optical axis of the ½ wavelength plate, is set as "γ", the emitted light from the phase difference adjustment section 306 receives rotation of "2γ" from the polarization direction of the incidence light. Due to this, the emitted light from the phase difference adjustment section 306 becomes, for example, elliptically polarized light where the deflection angle is "α1 (<α0)".

The emitted light from the phase difference adjustment section 306 is converted to almost completely linear polarized light by the second polarizing section 308. In the present embodiment, the second polarizing section 308 is configured to have a Glan-Thompson prism. As a result, without the optical path with regard to the incident light being changed, abnormal light flux components out of the normal light flux components and the abnormal light flux components are emitted as linearly polarized light. Due to this, the emitted light from the second polarizing section 308 becomes linearly polarized light where the deflection angle is "α1".

Due to the optical rotation of the subject S, the polarization surface of the linearly polarized light which is incident onto the subject S is rotated. In the present embodiment, the subject S is an aqueous solution with glucose as a main component. Since glucose is an optically active substance, the refractive indexes with regard to each of the left and right circularly polarized light are different. As a result, when the linearly polarized light is incident onto the subject S, a difference occurs in the speed of the left and right circularly polarized light which travels in the subject S. As a result, a phase difference occurs in the left and right circularly polarized light which passes through the subject S and the polarization plane of the transmitted light which is transmitted through the subject S is rotated from the linearly polarized light when incident.

In addition, since the internal structure of glucose is chiralic, a difference occurs in the degree of absorption with regard to left and right circularly polarized light when the circularly polarized light is absorbed. As a result, when the linearly polarized light is incident onto the subject S, the amplitude of the light of the left and right circularly polarized light (the magnitude of the light) changes due to the circular dichroism. As a result, the transmitted light which is transmitted through the subject S becomes light which has amplitudes which differ between left and right.

Due to the optical rotation and the circular dichroism, the phase and the amplitude of the light which is emitted from the subject S is different to when the light was incident. As a result, the incident light which was linearly polarized light is changed to elliptically polarized light by being transmitted through the subject S. That is, as shown in FIG. 2, the linear polarized light with the deflection angle of "α1" when incident onto the subject S becomes elliptically polarized light with a deflection angle of "φ" by being transmitted through the subject S. In consideration of the elliptically polarized light, the deflection angle "φ" will be described below as an elliptical azimuth angle "φ".

In the present embodiment, the transmitted light which is transmitted through the subject S is assumed to be elliptically polarized light and the polarization state of the transmitted light is measured by the feature values of ellipses being measured. Specifically, data is obtained on the detection voltages (Ex, Ey) of the light intensity which is detected by the light receiving section 320 while the light detecting section 314 is being rotated. Then, the detection voltages (Exmax, Eymax) where the intensity of the received light, which corresponds to the length of the major axis of ellipse, is the largest and the detection voltages (Exmin, Eymin) where the intensity of the received light, which corresponds to the length of the minor axis of ellipse, is the smallest are measured as feature values. Then, using these feature values, polarization parameter values which indicate the polarization state of the transmitted light are calculated.

That is, in a state where the light detecting section 314 is fixed, the light intensity which is detected by the light receiving section 320 is one data set of detection voltage (Ex, Ey). Data sets of the detection voltages (Ex, Ey) where the light intensity is detected while the rotation state of the light detecting section 314 changes in various ways and the locus of the intensity of the received light, which is drawn in an Ex-Ey plane, is observed.

In addition, in the present embodiment, initial correction is performed) (α1=145°) so that the deflection angle of the linearly polarized light which is incident onto the subject S is "45°". Specifically, in a state where the subject S is not arranged in the optical apparatus 3, the first polarizing section 304 is positioned so that "Ex=Ey". The reason for the deflection angle of the linearly polarized light to be "45°" is as follows.

In order to correctly measure the polarization state of the transmitted light, it is necessary that the intensity of the light (P wave and S wave) which is orthogonally separated by the orthogonal separating section 316 is correctly detected by the light receiving section 320. However, the voltage which is generated by a light detecting unit such as a photodiode is an extremely small value and is a level which can be buried in noise. Accordingly, it is necessary that even a slight change in light intensity is grasped as a large change in the voltage value.

The ratio "Y=Ey/Ex" of the detection voltages "Ex" and "Ey" will be considered. In a case where a hyperbolic curve of "Y=1/Ex" with "Ey=1" is considered, the hyperbolic curve slopes downward along with an increase in the value of Ex. In a range where the value of "Ex" is large, the value of "Y" hardly changes even if the value of "Ex" changes. However, in a range where the value of "Ex" is small, the value of "Y" changes considerably with only a small change in the value of "Ex".

Accordingly, by setting the ratio of "Ex" and "Ey" to be "1:1", it is possible for there is to a considerable change in "Y=Ey/Ex" with regard to a slight change in "Ex". That is, by performing the initial correction so that "Ex=Ey", a relative change in "Ey" with regard to "Ex" (a relative change in "Ex" with regard to "Ey") is clear in a case where the subject S is arranged and it is possible to improve the measurement accuracy of the polarization state.

Figure 3:
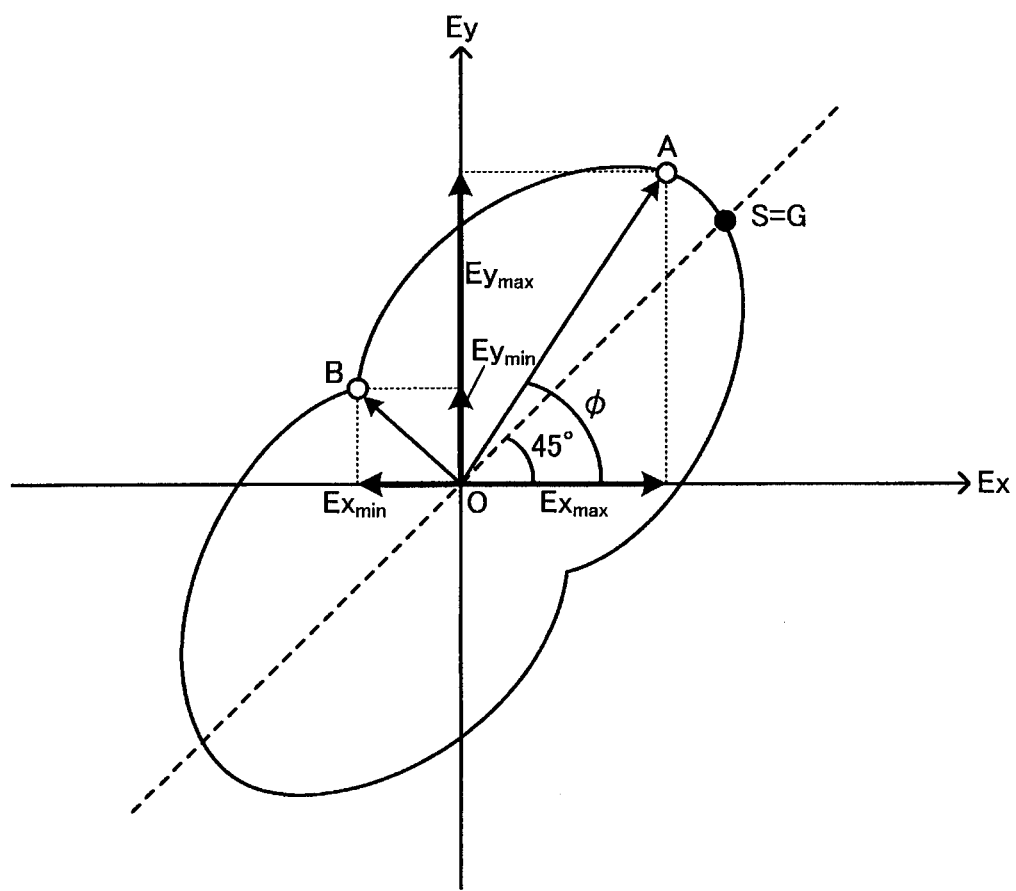
FIG. 3 is an explanatory diagram of the principles of polarization state measurement.

FIG. 3 is an explanatory diagram of a method for calculating the polarization parameter values. Here, a case is shown where the light detecting section 314 is rotated within an angular range of "0° to 360°". In FIG. 3, the vertical axis is the detection voltage "Ex" and the horizontal axis is the detection voltage "Ey". The locus of the detection voltages (Ex, Ey) which are sampled while the light detecting section 314 is being rotated is drawn as a solid line.

A start position S and an end position G of the rotation are positions where the deflection angle of the linearly polarized light which is incident on the subject S is "45°". The light detecting section 314 is rotated one with the start position S as a reference. By doing this, as shown in FIG. 3, for example, a locus with a peanut shape (a gourd shape) can be obtained. That a perfect elliptical locus is not shown is because, since components other than glucose are included in the subject S, it is assumed that there is an effect from the refractive indexes and transmission rates of these components.

Out of the data sets of the detection voltages (Ex, Ey), the data where the absolute value of the light intensity is the largest and the data where the absolute value of the light intensity is the smallest are measured as feature values of the ellipse. That is, the detection voltages (Exmax, Eymax) where "(Ex2+Ey2)1/2" is the largest and the detection voltages (Exmin, Eymin) where "(Ex2+Ey2)1/2" is the smallest are measured as feature values.

In FIG. 3, a point on the coordinates which are equivalent to (Exmax, Eymax) is shown as a point A with a white circle and a point on the coordinates which are equivalent to (Exmin, Eymin) is shown as a point B with a white circle. In the Ex-Ey plane, a vector OA where the origin O is a start point and the point A is an end point becomes a vector which is equivalent to the largest light intensity. In addition, a vector OB where the origin O is a start point and the point B is an end point becomes a vector which is equivalent to the smallest light intensity.

At this time, using the detection voltages (Exmax, Eymax) and (Exmin, Eymin), each of an ellipticity angle "θ" and an elliptical azimuth angle "φ" are calculated according to, for example, equations (1) and (2).

[Equation 1]

$$\theta = \tan^{-1}\left(\frac{\sqrt{Ex_{min}^2 + Ey_{min}^2}}{\sqrt{Ex_{max}^2 + Ey_{max}^2}}\right) \quad (1)$$

[Equation 2]

$$\phi = \tan^{-1}\left(\frac{Ey_{max}}{Ex_{max}}\right) \quad (2)$$

Here, in FIG. 3, the case where the light detecting section 314 is rotated within an angular range of "0° to 360°" is used as an example, but the angular range by which the light detecting section 314 is rotated is not limited to this. The elliptical locus which can be obtained by rotating the light detecting section 314 is symmetrical with a direction of "180°". As a result, if the light detecting section 314 is rotated by at least "180°", it is possible to reproduce the entire locus due to the symmetry thereof.

Figure 4:
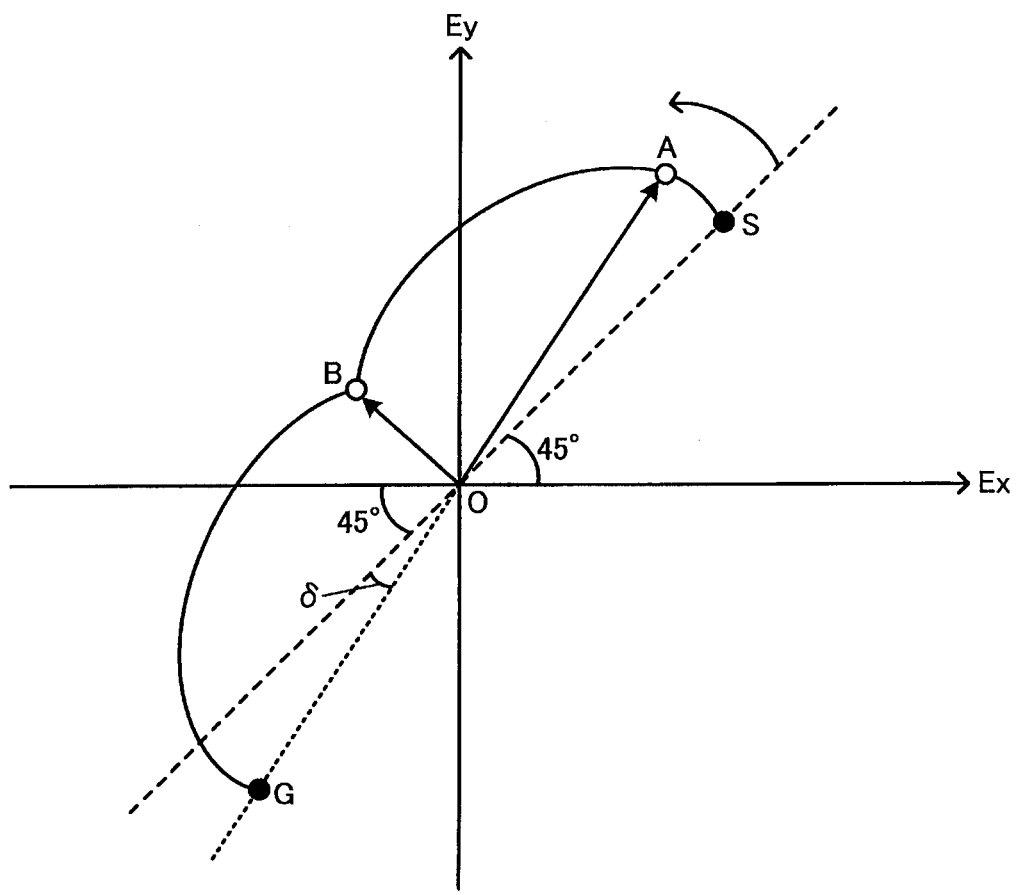
FIG. 4 is an explanatory diagram of the principles of polarization state measurement.

Therefore, as shown in FIG. 4, it is sufficient if the light detecting section 314 is rotated within, for example, an angular range of "0° to 180°+δ" with a margin of the amount of an angle "δ". That is, the light detecting section 314 is rotation controlled with a position with the deflection angle of "45°" as the start point S and a position with the deflection angle "225°+δ" as the end point G. Here, the value of "δ" is able to be arbitrarily selected, but it is sufficient if selected within a range of, for example, "0° to 10°".

Figure 5:
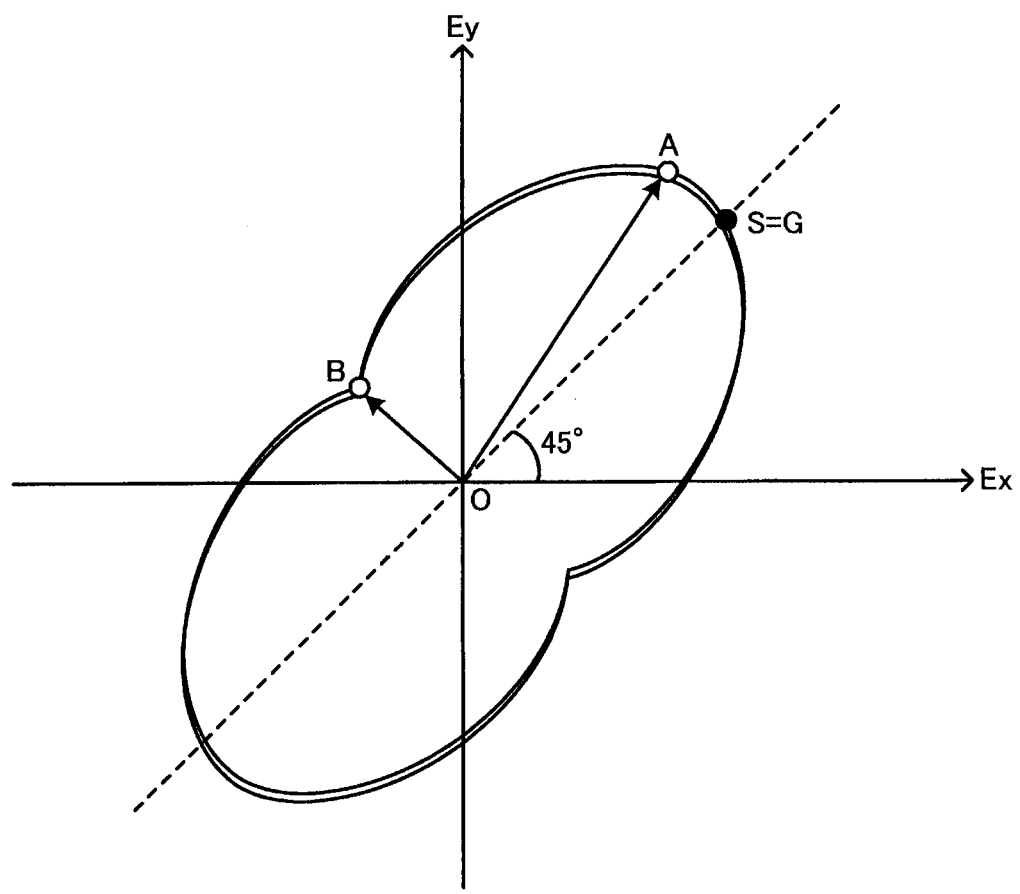
FIG. 5 is an explanatory diagram of the principles of polarization state measurement.

In addition, the light detecting section 314 may be rotated a plurality of times and not just be rotated once. Specifically, for example, as shown in FIG. 5, the light detecting section 314 may be rotation controlled within an angular range of "0° to 720°". That is, an elliptical locus is drawn by rotating the light detecting section 314 twice with the position with the deflection angle of "45°" as the start point S and the end point G. Naturally, the light detecting section 314 may be rotated three times or more by further widening the angular range of rotation.

Furthermore, in the case above, the direction in which the light detecting section 314 is rotated may be a constant direction or may be reversed during the rotation.

For example, in FIG. 4, in the case where the light detecting section 314 is rotation controlled within the angular range of "0° to 180°+δ", after the light detecting section 314 is rotation controlled in a first rotation direction (positive direction) over "0° to 180°+δ", the light detecting section 314 may be rotation controlled in a second rotation direction (negative direction) over "180°+δ to 0°".

In addition, in FIG. 5, in the case where the light detecting section 314 is rotated twice within an angular range of "0° to 720°", the light detecting section 314 may be rotation controlled in the first rotation direction (positive direction) in the first rotation and the light detecting section 314 may be rotation controlled in the second rotation direction (negative direction) in the second rotation.

3. Configuration of Calculation Apparatus 5

The calculation apparatus 5 is a control apparatus which performs control of the optical apparatus 3 and is also a calculation apparatus which calculates the polarization state of the transmitted light which is transmitted through the subject S based on the detection voltages (Ex, Ey) obtained from the light receiving section 320 of the optical apparatus 3.

As shown in FIG. 1, the calculation apparatus 5 is a computer system which is configured to be provided with a processing section 510, an input section 520, a display section 530, a sound output section 540, a communication section 550, and a storage section 560 and where each section is connected via a bus 580.

The processing section 510 is a control apparatus and a calculation apparatus which comprehensively controls each section of the calculation apparatus 5 and the optical apparatus 3 according to various programs such as a system program which is stored in the storage section 560 and is configured to have a processor such as a CPU (Central Processing Unit) or a DSP (Digital Signal Processor). The processing section 510 has a rotation control section 511 and a polarization state measurement section 513 as its important functional sections.

The rotation control section 511 controls the rotation of the light detecting section 314 using the rotation apparatus 330. Specifically, a rotation control signal, which rotation controls the light detecting section 314 in a rotation state which is determined in advance or a rotation state which is instructionally input by an inspector, is output to the rotation apparatus 330.

The polarization state measurement section 513 calculates and measures the polarization state of the transmitted light which is transmitted through the subject S based on the detection voltages (Ex, Ey) obtained from the light receiving section 320 of the optical apparatus 3. That is, the polarization parameter values are calculated according to equations (1) and (2).

The input section 520 is an input apparatus which is configured to have, for example, a keyboard, a button switch, or the like and a signal of a key or a button which has been pressed is output to the processing section 510. Each type of instructional input such as the input of various types of data and the instruction to start measuring the polarization state is carried out by the operation of the input section 520.

The display section 530 is a display apparatus which performs various types of display based on a display signal which is output from the processing section 510 and is configured to have, for example, a LCD (Liquid Crystal Display) or the like. Information such as the polarization state (the polarization parameter values), which is measured by the polarization state measurement section 513, are displayed in the display section 530.

The sound output section 540 is a sound output apparatus which performs output of sound based on a sound output signal which is output from the processing section 510 and is configured to have, for example, a speaker or the like. From the sound output section 540, audio guidance, an alarm sound, or the like is output according to the initial correction or measurement of the polarization state.

The communication section 550 is a communication apparatus for the calculation apparatus 5 to perform wired communication or wireless communication with external information processing apparatuses. The communication section 550 is configured to have, for example, a wired communication module which performs communication via a wired cable, a wireless communication module which performs communication with a wireless LAN, spread spectrum communication, or the like.

The storage section 560 is configured to have a storage apparatus (memory) such as a ROM (Read Only Memory), a flash ROM, or a RAM (Random Access Memory) and stores various types of programs for realizing a system program of the calculation apparatus 5, various types of functions such as a rotation control function and a polarization state measurement function, various types of data, and the like. In addition, the storage section 560 has a work area which temporarily stores data during processing, processing results, and the like for various types of processing.

A polarization state measurement program 561 which is read out by the processing section 510 and is executed as a polarization state measurement process (refer to FIG. 7) is stored in the storage section 560 as a program. The polarization state measurement program 561 includes a polarization parameter value calculation program 561A, which is executed as a polarization parameter value calculation process, as a subroutine. These processes will be described later in detail using a flowchart.

In addition, for example, light intensity data 563 and polarization state measurement data 565 are stored as data in the storage section 560.

Figure 6:
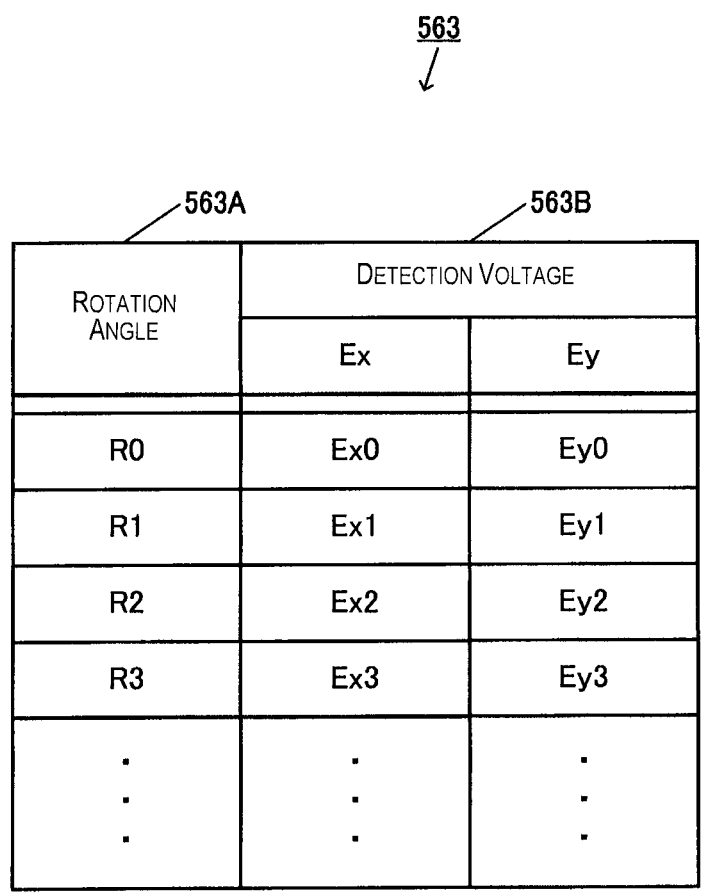
FIG. 6 is a data configuration diagram of light intensity data.

FIG. 6 is a diagram illustrating a data configuration example of the light intensity data 563. A rotation angle 563A and a detection voltage 563B are stored so as to correspond to each other in the light intensity data 563. The rotation angle 563A is a rotation angle when the rotation apparatus 330 rotates the light detecting section 314 and a rotation angle with a predetermined angular range is stored. In addition, the detection voltage 563B stores detection voltage (Ex, Ey) data which is obtained from the light receiving section 320 (a first light receiving section 320A and a second light receiving section 320B) with regard to each rotation angle 563A.

The polarization state measurement data 565 is measurement data which indicates the polarization state of the transmitted light which is measured in the polarization state measurement process. For example, ellipticity angle 565A and elliptical azimuth angle 565B, which are calculated using the polarization parameter value calculation process, are included in this.

4. Process Flow

Figure 7:
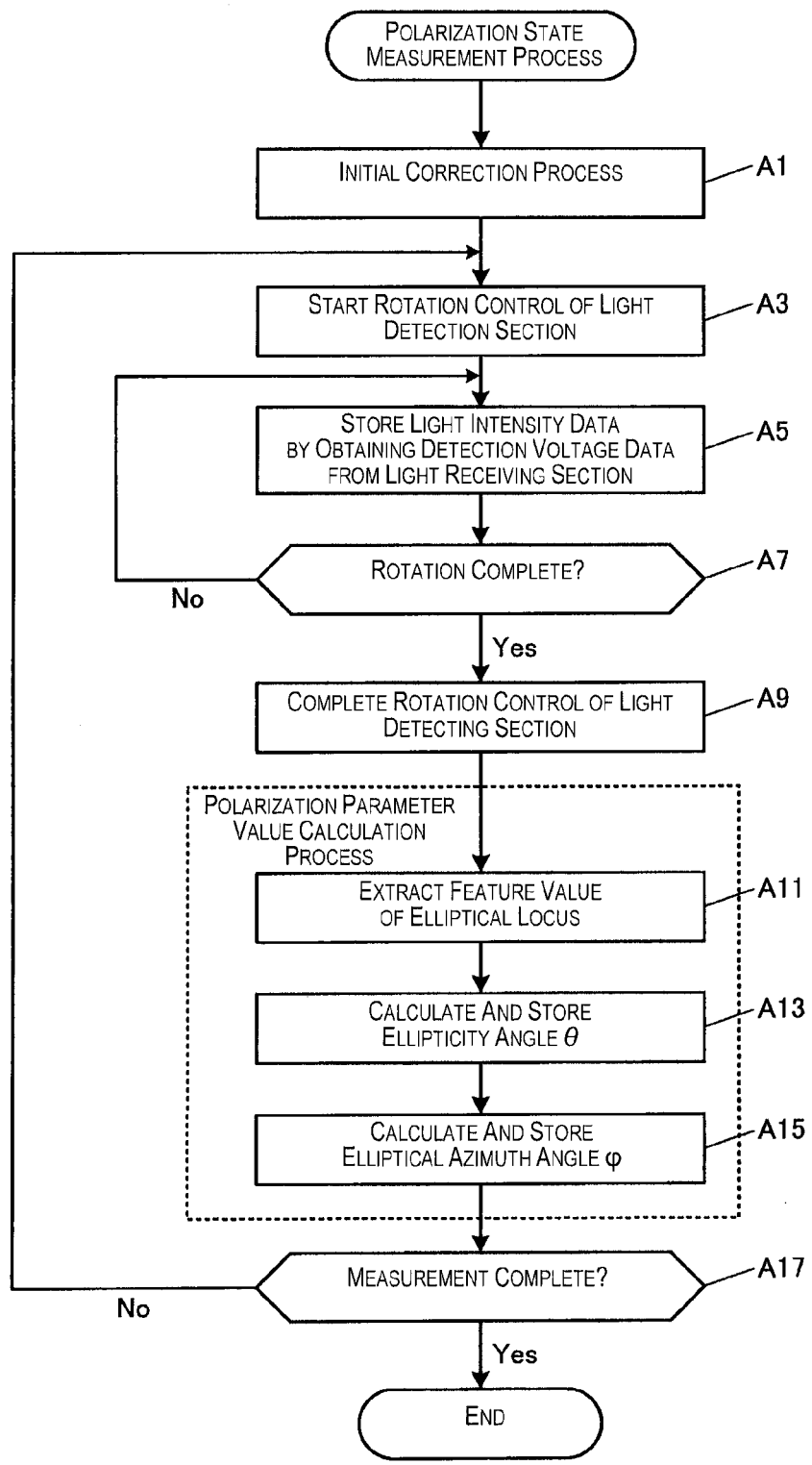
FIG. 7 is a flowchart illustrating the flow of a polarization state measurement process.

FIG. 7 is a flowchart illustrating the flow of a polarization state measurement process which is executed in the polarization state measurement apparatus 1 by the polarization state measurement program 561 which is stored in the storage section 560 being read out by the processing section 510.

Initially, the processing section 510 performs an initial correction process (step A1). Specifically, the inspector which performs inspection of the subject S is instructed to position the first polarizing section 304. The inspector positions the first polarizing section 304 and adjusts the deflection angle of the linearly polarized light which is incident onto the subject S according to the instruction. As a technique for adjusting the deflection angle, for example, the inspector is instructed to rotate the first polarizing section 304 so that the rotation plane is orthogonal with regard to the optical path. The inspector rotates the first polarizing section 304 while changing the rotation angle in small amounts according to the instruction.

At this time, the processing section 510 samples the detection voltages (Ex, Ey) which are output from the light receiving section 320 with regard to each rotation angle of the first polarizing section 304. Then, when "Ex=Ey" is detected, by an announcement or an alarm sound which reports this to the inspector being output from the sound output section 540, by a message which reports this being displayed on the display section 530, or the like, the successful adjustment of the deflection angle is reported to the inspector. Due to this, the initial correction is completed.

Next, the rotation control section 511 starts the rotation control of the light detecting section 314 (step A3). Then, the processing section 510 acquires the detection voltage (Ex, Ey) from the light receiving section 320 and stores it in the storage section 560 as the light intensity data 563 (step A5).

After this, the rotation control section 511 determines whether or not the rotation of the light detecting section 314 is complete (step A7), and in a case where the continuation of the rotation is determined (step A7; No), the rotation control continues and the process returns to step A5. In addition, in a case where the completion of the rotation is determined (step A7; Yes), the rotation control of the light detecting section 314 is completed (step A9).

Next, the processing section 510 performs a polarization parameter value calculation process according to the polarization parameter calculation program 561A which is stored in the storage section 560 (steps A11 to A15).

The polarization state measurement section 513 extracts the feature values of the elliptical locus (step A11). Specifically, the light intensity data 563 of the storage section 560 is referenced and the detection voltage (Ex, Ey) data which is equivalent to the largest light intensity and the smallest light intensity is extracted as the feature values of the elliptical locus. The transmitted light which is transmitted through the subject S is assumed to be elliptically polarized light and this is equivalent to the measuring of the feature value of the ellipse.

Then, the polarization state measurement section 513 calculates the ellipticity angle 565A according to equation (1) using the feature values which are extracted and stores in the storage section 560 as the polarization state measurement data 565 (step A13). In addition, the polarization state measurement section 513 calculates the elliptical azimuth angle 565B according to equation (2) using the feature values which are extracted and stores it in the storage section 560 as the polarization state measurement data 565 (step A15). Then, the polarization state measurement section 513 completes the polarization parameter value calculation process.

Next, the processing section 510 determines whether or not the measurement of the polarization state is complete (step A17), and in a case where the continuation of the measurement is determined (step A17; No), the process returns to step A3. In addition, in a case where the completion of the measurement is determined (step A17; Yes), the polarization state measurement process is completed.

5. Operational Effects

In the polarization state measurement apparatus 1, the optical apparatus 3 has the light detecting section 314 which detects light and emits the transmitted light where the linearly polarized light, which is emitted from the light source 300 and is converted by the second polarizing section 308, is transmitted through the subject S. In addition, the optical apparatus 3 has the orthogonally separating section 316 which orthogonally separates the emitted light from the light detecting section 314 and the light receiving section 320 which receives the light which is orthogonally separated using the orthogonal separating section 316. The calculation apparatus 5 outputs the rotation control signal to the rotation apparatus 330 and rotation controls the light detecting section 314 so that the rotation plane is orthogonal with regard to the optical path of the transmitted light. Then, the calculation section 5 measures the polarization state of the transmitted light which is transmitted through the subject S using the intensity with which the light, which is orthogonally separated by the orthogonally separating section 316 during the rotation of the light detecting section 314, is received by the light receiving section 320.

Due to the circular dichroism and optical rotation of the subject S, the transmitted light where linearly polarized light is transmitted through the subject S is converted to elliptically polarized light. Therefore, the transmitted light where linearly polarized light is transmitted through the subject S is assumed to be elliptically polarized light and the polarization state is measured by measuring the feature values of the ellipse. By measuring the voltage value where the intensity of the light received by the light receiving section 320 is the largest and the voltage value where the intensity of the light received by the light receiving section 320 is the smallest as the feature values, it is possible to calculate the polarization parameter values such as the ellipticity angle and the elliptical azimuth angle which determine the shape of the ellipse.

Optical system errors, which depend on the accuracy of the polarizers and the prisms which configure the optical apparatus 3, the optical system assembly errors, and the like, are present in the intensity of the light which is received by the receiving section 320. Accordingly, even if the intensity of the received light is measured in a state where the light detecting section 314 is fixed, there is no guarantee that this will necessarily match with the apexes in the longitudinal direction of the ellipse. However, in the present embodiment, it is possible to exactly determine the apexes in the longitudinal direction and the latitudinal direction of the ellipse by drawing the locus of the intensity of the light received by the light receiving section 320 while the light detecting section 314 is being rotated.

Normally, the optical system assembly errors depend on the positioning of each optical element. Whether or not the optical axes of the polarizing prisms and the light concentrating lenses are lined up in a straight line has the largest effect in terms of the positioning. In a case where the optical axes are not straight, since the transmitted light which is transmitted through the subject S is not exactly connected to a focal point on the light receiving section 320 (photodiode) and the voltage which is to be originally generated is not able to be detected in the light receiving section 320, the performing of so-called optical axis adjustment is necessary.

It is possible to realize the optical axis adjustment by, for example, grasping a change in the focal position of the optical system while changing the position and the orientation of the optical elements which configure the optical system, but there is a mechanical limitation to this. In the present embodiment, it is possible to grasp the optical system errors, which are not dealt with by the optical axis adjustment method of the related art, in the form of the locus which is drawn by the intensity of the received light. That is, by drawing out the locus of the intensity of the light which is received by the light receiving section 320 while the light detecting section 314 is rotated in various rotation states (rotation angle, rotation direction, and number of rotations), it is possible to correctly measure the polarization state of the transmitted light which is transmitted through the subject S in a form which includes the optical system errors.

The polarization state measurement apparatus 1 of the present embodiment is able to be used by being, for example, built into a measurement unit such as a sugar content measurement apparatus which measures the sugar content of fruit or a blood sugar level measurement apparatus which measures the blood sugar level of a person. In a case of being applied to the sugar content measurement apparatus, experiments are performed to set the optical apparatus 3 with fruit as the subject S. In addition, in a case of being applied to the blood sugar level measurement apparatus, linearly polarized light is irradiated onto a measurement portion with an ear lobe, a finger tip, the outer skin of a finger, or the like of a person as the measurement portion and the polarization state of the transmitted light is measured. Then, the blood sugar level (glucose concentration) of the person who is the subject S is measured based on the polarization parameter values such as the ellipticity angle and the elliptical azimuth angle which are measured as the polarization state.

6. Modified Example

The embodiments where the present invention can be applied are not limited to the embodiment described below, and naturally, various modifications are possible within the scope which does not depart from the gist of the present invention. Below, modified examples will be described.

6-1 Determining Vibration Locus of Transmitted Light

In the embodiment described above, the vibration locus of the transmitted light is determined based on the locus which is drawn out by the detection voltages of the light intensity of the received light which is received by the light receiving section 320 in the case where the light detecting section 314 is rotated. However, the method for determining the vibration locus is not limited to this.

For example, a method (1) for determining the vibration locus which uses pattern matching may be applied. Specifically, data on a plurality of elliptical patterns (referred to below as "elliptical pattern data") is input into a database in advance in the storage section 560 based on various types of parameter values which determine the shape of an ellipse such as the length of the major axis, the length of the minor axis, the ellipticity angle, and the elliptical azimuth angle of the ellipse. It is possible to set the elliptical pattern data as a data set of, for example, the light intensity according to the elliptical shape.

In this case, a pattern matching process is performed with the data sets of the light intensity of the received light, which is obtained by the light receiving section 320 in the case where the light detecting section 314 is rotated, and the plurality of types of elliptical pattern data which is input into the database. Then, the elliptical locus which is determined using the elliptical pattern data, where it is determined that the goodness of fit is high using the pattern matching process, is determined to be the vibration locus of the transmitted light which is transmitted through the subject S.

In addition, as another method, a method (2) for determining the vibration locus which uses an averaging process may be applied. Specifically, the light detecting section 314 is rotated for a plurality of rotations with the rotation direction being constant or the rotation direction being reversed. By the light detecting section 314 being rotation for N rotations, data sets of the light intensity can be obtained for the N rotations. Then, the data sets of the light intensity for N rotations is processed to be average (for example, an arithmetic mean) and the locus, which is determined using the data set of the light intensity which is obtained as a result of the average process, is determined as the vibration locus of the transmitted light which is transmitted through the subject S.

Figure 8:
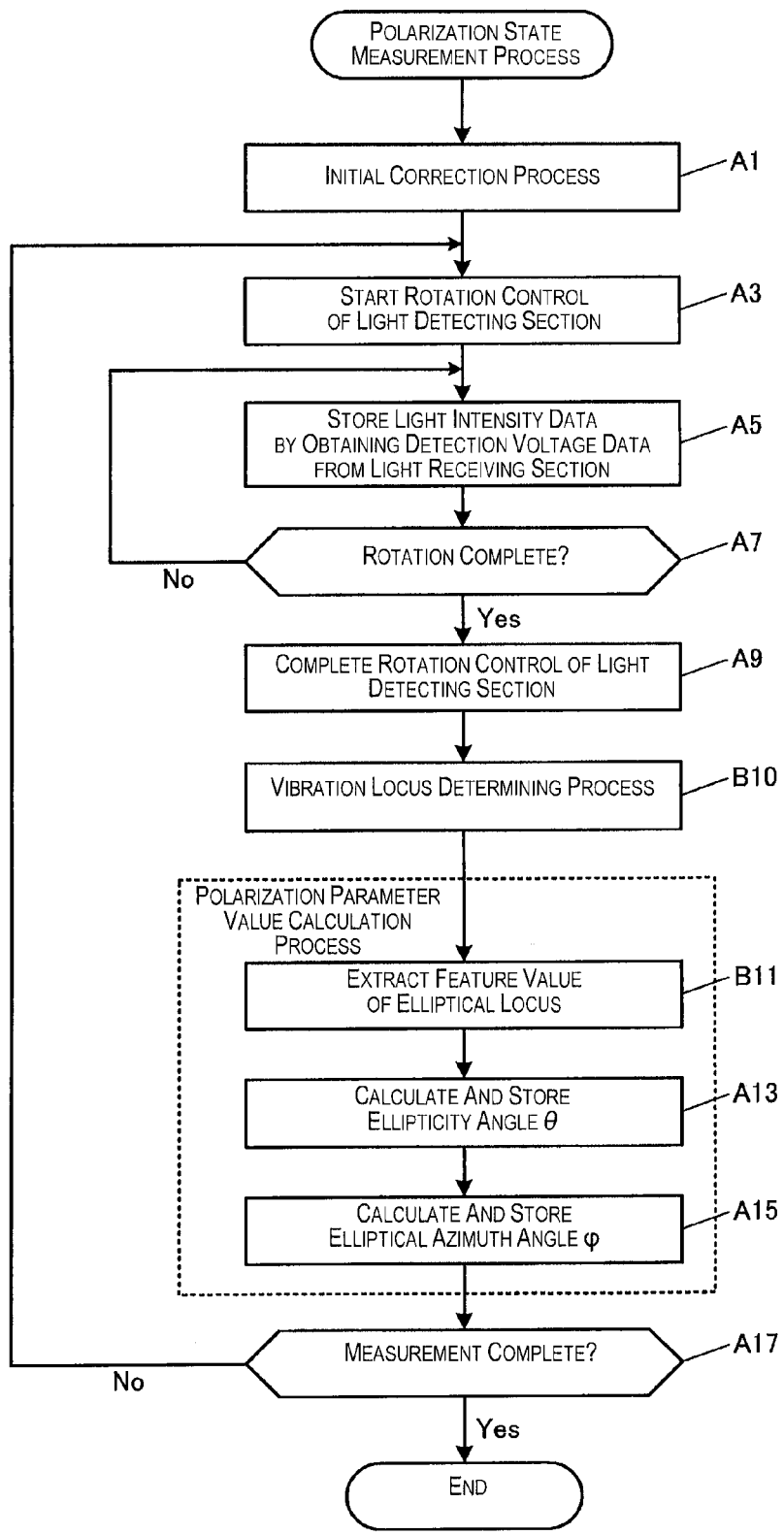
FIG. 8 is a flowchart illustrating the flow of a second polarization state measurement process.

FIG. 8 is a flowchart illustrating the flow of a second polarization state measurement process which the processing section 510 of the calculation apparatus 5 executes instead of the polarization state measurement process of FIG. 7 in the modified example. Here, the same reference numerals are attached to the same steps as the polarization state measurement process and the description is omitted. The diagrammatical representation is omitted, but in the present modified example, the processing section 510 has the vibration locus determining section, which determines the vibration locus of the transmitted light using the intensity of the received light of the light receiving section 320, as a functional section.

After the rotation control of the light detecting section 314 is completed in step A9, the vibration locus determining section performs a vibration locus determining process (step B10). It is possible for the vibration locus determining process to be realized as a process where the method (1) for determining the vibration locus which uses the pattern matching or the method (2) for determining the vibration locus which uses the averaging process as described above are applied.

After that, the polarization state measurement section 513 extracts the feature values of the vibration locus which is determined in the vibration locus determining process of step B10 (step B11). Specifically, out of the data sets of the light intensity which show the vibration locus which is determined in the vibration locus determining process, the data which corresponds to the largest light intensity and the smallest light intensity are extracted as the feature values of the ellipse. Then, the ellipticity angle "θ" and the elliptical azimuth angle "ϕ" are calculated using the feature values which are extracted.

6-2. Measuring Feature Values of Ellipse

In the embodiment described above, out of the detection voltages (Ex, Ey) of the light receiving section 320, the detection voltages (Exmax, Eymax) which correspond to the largest light intensity and the detection voltages (Exmin, Eymin) which correspond to the smallest light intensity are measured as the feature values. Other than these, the following may also be measured as the feature values.

In the coordinates plane of the detection voltages (Ex, Ey), two vectors of a first feature value vector OA where the origin O is a start point and the point A on the elliptical locus is an end point and a second feature value vector OB where the origin O is a start point and the point B on the elliptical locus is an end point will be considered. At this time, the first feature value A and the second feature value B are selected so that an angle formed from the first feature value vector OA and the second feature value vector OB is "90°".

Specifically, for example, out of the combinations of the feature values A and B where the angle formed from the first feature value vector OA and the second feature value vector OB is "90°", a combination is determined so that the difference in the magnitude of the two vector is the largest. That is, a combination of the feature values is determined so that |OA|-|OB| is the largest and the polarization state is measured using the feature values A and B which are included in this combination.

Here, the method for measuring the feature values of the ellipse is able to be applied similarly in practice to a case where the vibration locus determining method described above is applied. Specifically, in the second polarization state measuring processing of FIG. 8, after the vibration locus determining process is performed in step B10, the polarization state measurement section 513 extracts the combination of the feature values A and B which satisfy the condition described above as the feature values from among the vibration locus which is determined in the vibration locus determining process (step B11).

6-3. Polarization Parameter Value Calculation Method

In the embodiment described above, the polarization parameter values are calculated according to equations (1) and (2) but the method of calculating the polarization parameter values is not limited to this. For example, it is possible to calculate the polarization parameter values according to equation (3) and (4).

[Equation 3]

$$\theta = \tan^{-1}\left(\frac{Ex_{min} + Ey_{min}}{Ex_{max} + Ey_{max}}\right) \quad (3)$$

[Equation 4]

$$\phi = \tan^{-1}\left(\frac{Ey}{Ex}\right)^{\frac{1}{2}} : (Ex + Ey) = \text{Max} \quad (4)$$

6-4. Deflection Angle of Linearly Polarized Light

In the embodiment described above, the deflection angle of the linearly polarized light which is incident onto the subject S is set as "45°", but this is one design for improving the accuracy of the measuring of the polarization state and it is not necessary for the deflection angle to necessarily be "45°".

In addition, in the embodiment described above, the initial correction is performed by positioning the first polarizing section 304 which is arranged at the front of the subject S, but the initial correction may be performed by positioning the light detecting section 314 which is arranged at the rear of the subject S. In this case, for example, the light detecting section 314 is rotated so that the rotation plane is orthogonal with regard to the optical path. Then, the light detecting section

314 may be rotation controlled with the setting angle of the light detecting section 314 where "Ex=Ey" is satisfied as a reference.

6-5. Polarization Optical Element

In the embodiment described above, the second polarizing section 308 and the light detecting section 314 are described as being configured to have a Glan-Thompson prism, but naturally, may be configured to have a polarization optical element other than this. For example, the second polarizing section 308 and the light detecting section 314 may be configured to have a Glan-Taylor prism which is a polarization optical element which is the same Glan type.

In addition, in the embodiment described above, the orthogonal separating section 316 is described as being configured to have a Wollaston prism, but it is possible to also appropriately modify the polarization optical element which configures the orthogonal separating section 316. For example, there may be a configuration where the orthogonal separating section 316 has a polarization optical element which has an orthogonal separating function which is a Glan-laser prism or a lotion prism.

What is claimed is:

1. A polarization state measurement apparatus adapted to measure polarization state of light emitted from a light source after the light is linearly polarized and transmitted through a subject, comprising:
    a light detecting section operatively coupled to the light source and rotatably arranged at a position opposite from the light source with respect to the subject to detect the linearly polarized light transmitted through the subject;
    an orthogonal separating section operatively coupled to the light detecting section to orthogonally separate the emitted light from the light detecting section;
    a light receiving section operatively coupled to the orthogonal separating section to receive light which is orthogonally separated by the orthogonal separating section; and
    a processing section including
        a rotation control section programmed to control rotation of the light detecting section so that the rotation plane is orthogonal with regard to an optical path of the transmitted light, and
        a polarization state measuring section programmed to measure the polarization state of the transmitted light using the intensity with which the light, which is orthogonally separated during the rotation of the light detecting section, is received by the light receiving section.

2. The polarization state measurement apparatus according to claim 1,
    wherein the rotation control section is programmed to rotate the light detecting section within a predetermined angular range.

3. The polarization state measurement apparatus according to claim 1,
    wherein the polarization state measuring section has a vibration locus determining section programmed to determine a vibration locus of the transmitted light using the intensity of the light which is received and measure the polarization state of the transmitted light using the vibration locus which is determined by the vibration locus determining section.

4. The polarization state measurement apparatus according to claim 1,
    wherein the polarization state measuring section is programmed to measure the polarization state by the transmitted light being assumed to be elliptically polarized light and the feature values of ellipses being measured.

5. The polarization state measurement apparatus according to claim 1,
    wherein the linearly polarized light has a deflection angle of 45°.

6. The polarization state measurement apparatus according to claim 1,
    wherein the light detecting section has a Glan-Thompson prism.

7. The polarization state measurement apparatus according to claim 1,
    wherein the orthogonally separating section has a Wollaston prism.

8. A polarization state measuring method, which is a method for measuring polarization state of light emitted from a light source after the light is linearly polarized and transmitted through a subject by controlling an optical apparatus provided with a light detecting section operatively coupled to the light source and rotatably arranged at a position opposite from the light source with respect to the subject to detect the linearly polarized light transmitted through the subject, an orthogonal separating section operatively coupled to the light detecting section to orthogonally separate, the emitted light from the light detecting section, and a light receiving section operatively coupled to the orthogonal separating section to receive light which is orthogonally separated by the orthogonal separating section, the method comprising:
    rotating the light detecting section so that the rotation plane is orthogonal with regard to an optical path of the transmitted light; and
    measuring the polarization state of the transmitted light using the intensity with which the light, which is orthogonally separated during the rotation of the light detecting section, is received by the light receiving section.

* * * * *